United States Patent
Schroering

(10) Patent No.: US 6,379,153 B1
(45) Date of Patent: Apr. 30, 2002

(54) DENTAL IMPLANT HAVING A DUAL-TEXTURED EXTERIOR SURFACE

(76) Inventor: Robert L. Schroering, Dental Implant Center, 3950 Kresge Way, Suite 403, Louisville, KY (US) 40207

(*) Notice: Subject to any disclaimer, the term of this patent is extended or adjusted under 35 U.S.C. 154(b) by 0 days.

(21) Appl. No.: 09/689,185

(22) Filed: Oct. 12, 2000

Related U.S. Application Data

(60) Provisional application No. 60/159,485, filed on Oct. 14, 1999.

(51) Int. Cl.$^7$ .................................................. A61C 8/00
(52) U.S. Cl. ........................................ 433/173; 433/174
(58) Field of Search ................................. 433/173, 174, 433/175, 176, 201.1

(56) References Cited

U.S. PATENT DOCUMENTS

| | | |
|---|---|---|
| 4,206,516 A | 6/1980 | Pilliar |
| 4,547,327 A | 10/1985 | Bruins et al. .................. 264/16 |
| 4,713,003 A | 12/1987 | Symington et al. .......... 433/173 |
| 4,713,004 A | 12/1987 | Linkow et al. .............. 433/174 |
| 4,960,381 A | 10/1990 | Niznick ........................ 433/173 |
| 5,049,074 A | 9/1991 | Otani et al. .................. 433/173 |
| 5,236,458 A | 8/1993 | Ducheyne .................... 623/16 |
| 5,269,685 A | 12/1993 | Jorneus ........................ 433/174 |
| 5,344,457 A | 9/1994 | Pilliar et al. .................. 623/16 |
| 5,370,692 A | 12/1994 | Fink et al. .................... 623/16 |
| 5,427,527 A | 6/1995 | Niznick et al. .............. 433/174 |
| 5,433,606 A | 7/1995 | Niznick et al. .............. 433/173 |
| 5,478,237 A * | 12/1995 | Ishizawa .................. 433/201.1 |
| 5,484,286 A | 1/1996 | Hansson .................. 433/201.1 |
| 5,571,017 A | 11/1996 | Niznick ........................ 433/174 |
| 5,591,029 A | 1/1997 | Zuest ........................... 433/173 |
| 5,601,429 A | 2/1997 | Blacklock .................... 433/174 |
| 5,603,338 A | 2/1997 | Beaty ........................... 623/16 |
| 5,685,715 A | 11/1997 | Beaty et al. .................. 433/173 |
| 5,695,336 A | 12/1997 | Lazzara ........................ 433/173 |
| 5,709,547 A | 1/1998 | Lazzara et al. .............. 433/174 |
| 5,727,943 A | 3/1998 | Beaty et al. .................. 433/174 |
| 5,755,574 A | 5/1998 | D'Alise ........................ 433/173 |
| 5,759,035 A | 6/1998 | Ricci ............................ 433/174 |
| 5,766,009 A | 6/1998 | Jeffcoat ........................ 433/173 |
| 5,863,201 A | 1/1999 | Lazzara et al. ........... 433/201.1 |
| 5,885,079 A | 3/1999 | Niznick ........................ 433/174 |
| 5,915,967 A | 6/1999 | Clokie .......................... 433/173 |
| 5,926,685 A | 7/1999 | Krebs et al. .................... 419/2 |
| 5,989,027 A | 11/1999 | Wagner et al. .............. 433/173 |
| 6,095,817 A | 8/2000 | Wagner et al. .............. 433/173 |
| 6,102,703 A | 8/2000 | Day .............................. 433/174 |

OTHER PUBLICATIONS

Adell, R. et al, A 15–year study of osseointegrated implants in the treatment of the edentulous jaw, Int. J. Oral Surg., 1981, pp. 387–416, v. 10, Munksgaard, Copenhagen, Denmark.

* cited by examiner

Primary Examiner—John J. Wilson
(74) Attorney, Agent, or Firm—Joan L. Simunic; Middleton Reutlinger

(57) ABSTRACT

The present development relates to a dental implant having a dual-textured exterior surface. The implant has a smooth-surfaced head with a wrench-engaging projection, a tapered beaded-surfaced body for improved anchoring in bone, and a threaded transition region between the head and body that serves to anchor the implant to the bone and provides a barrier between the smooth surface of the head and the beaded surface of the body.

13 Claims, 1 Drawing Sheet

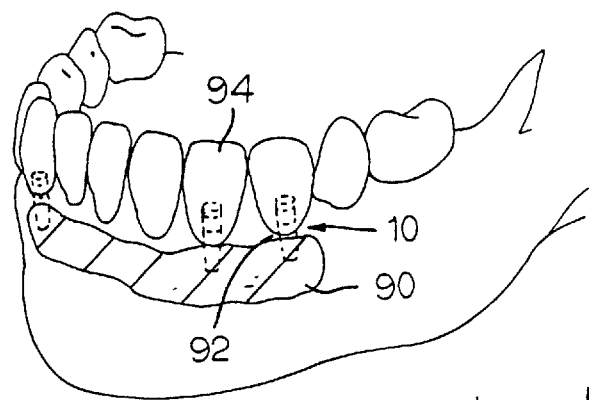
FIG. 1
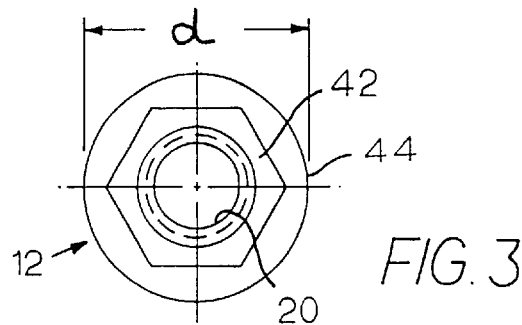
FIG. 3
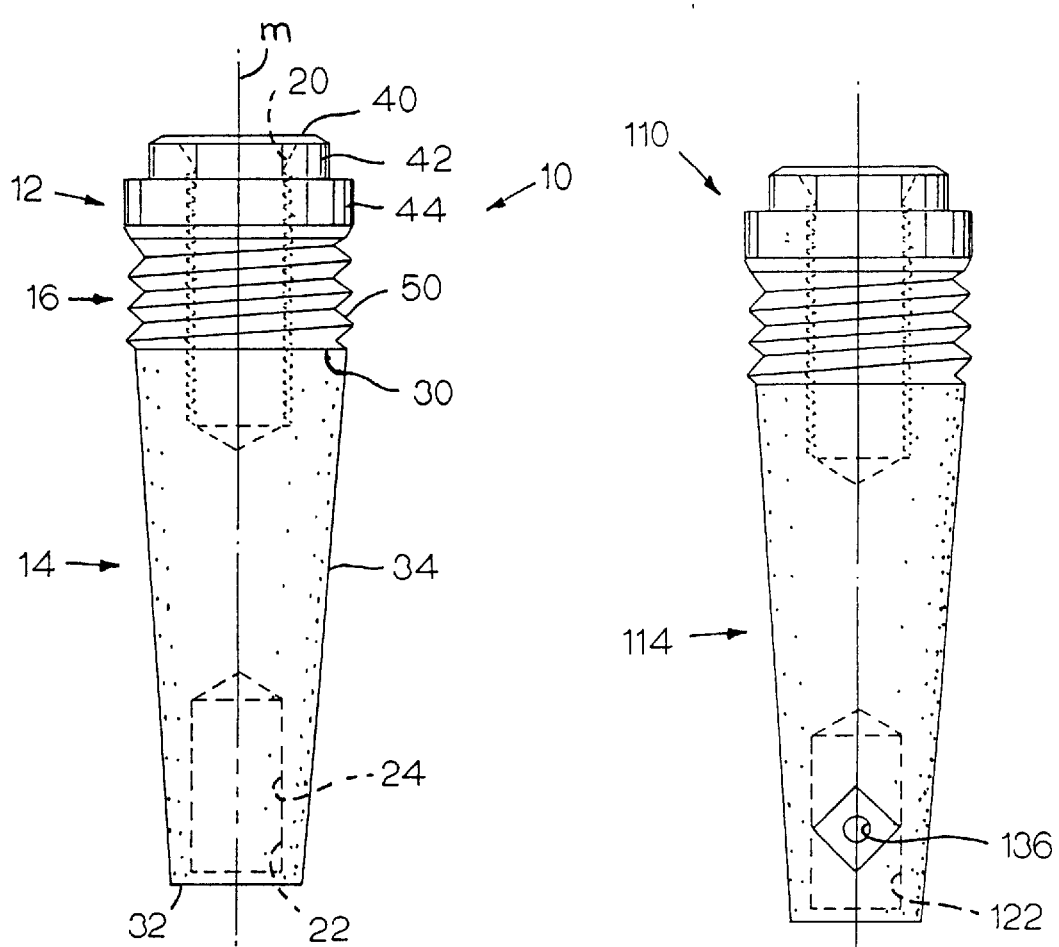
FIG. 2
FIG. 4

DENTAL IMPLANT HAVING A DUAL-TEXTURED EXTERIOR SURFACE

CROSS-REFERENCE TO RELATED APPLICATION

This application claims priority from U.S. Provisional Application Ser. No. 60/159,485, filed Oct. 14, 1999, which application is incorporated herein by reference in its entirety.

BACKGROUND

The present invention relates to a dental implant, and more particularly to a dental implant having a dual-textured exterior surface.

Dental implants are embedded in the jaw bone and serve to anchor one or more artificial teeth or dentures. Important to the success of such devices is the rigid anchoring of the implant in the bone, and several journal articles and patents have proposed various methods for achieving rigid anchoring (see U.S. Pat. No. 5,344,457, incorporated herein by reference). For example, U.S. Pat. No. 4,713,003, issued to Symington et al. describes an implant that has a tapered external body, resulting in a better distribution of the stresses acting on the device in situ than was achieved with cylindrical body implants. U.S. Pat. No. 5,344,457, issued to Pilliar et al, describes an implant that has a body with a non-porous surface on the upper portion of the implant and a porous surface on the lower portion of the implant. The porous surface provides interstices into which bone is permitted to grow once the implant is accommodated within the bone. As reported in U.S. Pat. No. 5,603,338, issued to Beaty, and incorporated herein by reference, roughening the surface of the implant can also aid in anchoring the implant because osteoblast-like cells attach more readily to the roughened surface than to a smooth surface.

While roughening the surface can improve the anchoring of the dental implant, the roughened surface also tends to attract and to retain bacteria which can result in infection of the tissue surrounding the implant site, particularly after the bone has receded slightly from the top edge of the implant as is commonly noted by dentists practicing implantology. Theoretically, this problem can be minimized by having an implant with a smooth or a non-porous upper portion, as described in the '457 patent. However in practice, when the implant of the '457 patent is embedded in the jaw bone, the bone tends to recede along the entire area adjacent to the non-porous upper portion allowing bacteria to accumulate at the interface of the non-porous upper portion and the porous lower portion of the implant. The interstices of the porous portion that permitted bone to connect the implant to the bone now also permit bacteria to burrow into the implant site causing deep-rooted infection and frequently the need for a second surgical procedure.

Thus, it would be beneficial to have a dental implant that includes a porous or beaded lower portion for strong anchoring to the bone and a non-porous portion that prevents bacterial accumulation, the non-porous portion being designed such that bacteria does not easily reach the porous or beaded portion of the implant.

SUMMARY OF THE PREFERRED EMBODIMENT

The present invention relates to a dental implant having a smooth-surfaced head, a tapered beaded-surfaced body, and a threaded transition region between the head and body. The beaded or porous surface of the body provides interstices into which bone is permitted to grow once the implant is accommodated within the jaw bone. The head has a wrench-engaging projection, and a smooth exterior surface so that bone anchoring and bacterial accumulation will be deterred. Between the head and the body is a threaded transition region that serves to anchor the implant to the jaw bone, and to provide a barrier between the smooth surface of the head and the beaded surface of the body thereby reducing the bacterial accumulation adjacent to the beaded surface.

DESCRIPTION OF FIGURES

FIG. 1 is a perspective view of a dental implant made in accordance with the present invention anchored in a lower jaw bone;

FIG. 2 is a side view of the dental implant of FIG. 1;

FIG. 3 is a top view of the dental implant of FIG. 1; and

FIG. 4 is a perspective view of an alternative embodiment of a dental implant made in accordance with the present invention.

DETAILED DESCRIPTION OF THE PREFERRED EMBODIMENT

The dental implants depicted in the various Figures are selected solely for the purposes of illustrating the invention. Other and different dental implants may utilize the inventive features described herein as well.

Reference is first made to FIGS. 1 through 3 in which the dental implant constructed in accordance with the present invention is generally noted by the character numeral 10. The dental implant 10 has as major components a head 12, a body 14, a threaded transition region 16, a bore 20, and a cavity 22. As shown in FIG. 1, the implant 10 is mounted in a cavity 92 bored into the jaw bone 90 of the patient such that the body 14 extends into the jaw bone 90. After the implant 10 is anchored in the jaw bone 90, a bridge or artificial tooth 94 can be secured to the implant 10 as is known in the art. The implant 10 can be formed from any smooth hard material commonly known in the art as being suitable for dental implants. In the preferred embodiment, the implant 10 is machined from a titanium alloy.

As shown in FIGS. 2 and 3, the dental implant 10 has a tapered body 14 of frusto-conical shape delimited by a top 30 and a bottom 32. The top 30 is adjacent to the threaded transition region 16. In the preferred embodiment, the taper angle of the body 14 is preferably a Morse taper, i.e. a taper angle of less than about 8°, and most preferably the taper angle of the body 14 is approximately 7°. The body 14 has a porous or beaded exterior surface 34 formed of a network of discrete particles. The beaded surface 34 provides interstices into which bone is permitted to grow once implant 10 is accommodated within the bone 90 (FIG. 1). The discrete particles of beaded surface 34 are preferably formed from the same titanium alloy from which implant 10 is formed, although other non-biodegradable, non-toxic, tissue-compatible materials may be used which admit of adherence to the material from which the implant 10 is formed. Examples of such other materials include cobalt-chromium beads, hydroxyapatite, aluminum oxide and ceramic materials known in the art. U.S. Pat. No. 5,344,457, which is incorporated herein by reference, describes a dental implant that include a porous or beaded surface similar to the surface 34 of implant 10, and a procedure for preparing the beaded surface. From the bottom 32 a cavity 22 extends longitudinally along a midline "m" into but not through the tapered body 14. The cavity 22 receives bone chips and fluid formed as the implant 10 is inserted into the jaw cavity 92. In the preferred embodiment, the cavity 22 has smooth interior surface walls 24, but the walls may have a roughened interior surface if required for the particular application.

The head 12 of the implant 10 defines a projection 42 with a top planar surface 40, and a neck 44. The exterior surfaces of the projection 42 and neck 44 are smooth so that bone anchoring and bacterial accumulation will be deterred. The neck 44 abuts the threaded transition region 16, and preferably has a rounded periphery with an exterior diameter "d" essentially equal to the diameter of the threads of the transition region 16. The projection 42 extends from the neck 44 away from the body 14, and serves as a wrench-engaging surface for the implant specialist and as a key for aligning the artificial tooth 94. Preferably the projection 42 has a periphery that defines a hexagonal shape, although other shapes may be defined as necessary to accommodate commercially available implantation tools. In the preferred embodiment, the projection 42 is tapered slightly as it approaches the top planar surface 40, although the tapering is not a required feature of the development. From the top surface 40 a bore 20 extends vertically into but not through the implant 10 along the midline "m". The bore 20 is preferably screw-threaded so as to engage a retaining screw (not shown) to secure the bridge or artificial tooth 94 to the implant 10.

As shown in FIG. 2, between the head 12 and body 14 is a transition region 16 having a threaded exterior surface 17. The threads 50 serve to anchor the implant 10 to the jaw bone 90. In addition, the threads 50 provide a barrier between the smooth surface of the neck 44 and the beaded surface 34 of the body 14 thereby reducing the bacterial accumulation adjacent to the beaded surface 34. The exterior surface 17 of the transition region 16 can be smooth—similar to the head 12, beaded—similar to the body 14, or roughened by other techniques known in the art, and in the preferred embodiment, the surface 17 is smooth. The number of threads 50 in the threaded region 16 can vary, but 3 to 5 threads is preferable.

An alternative embodiment of a dental implant 110 made in accordance with the present invention is shown in FIG. 4. The dental implant 110 is essentially identical to the implant 10 except that a through-hole 136 passes through the side walls of the body intersecting the cavity 122. The through-hole 136 allows new bone to grow through and into the cavity 122 in order to firmly anchor the implant 110 in the patient's jaw bone 90.

It is understood that, in light of a reading of the foregoing description and drawings, those with ordinary skill in the art will be able to male changes and modifications to the present invention without departing from the spirit or scope of the invention, as defined herein.

What is claimed is:

1. A dental implant for anchoring in bone, said implant having a longitudinal midline and comprising:
   a. a body, defining a top and a bottom, said body being non-threaded and having a frustoconical shape which is wider at the top than at the bottom and having an exterior surface formed from a network of discrete particles that create interstices along the surface;
   b. a transition region, having a threaded exterior surface, abutting the top of said body;
   c. a head, having a neck abutting said transition region and having a wrench-engaging projection extending from the neck away from said transition region, the projection defining a top planar surface, and the neck and the projection having smooth exterior surfaces; and
   d. a bore which protrudes along the midline from the top surface of the head projection through said head and through said transition region and into said body, said bore terminating within said body.

2. The implant of claim 1 wherein said implant is made from titanium alloy.

3. The implant of claim 1 wherein said body is tapered at a taper angle of less than 8°.

4. The implant of claim 1 wherein the discrete particles are formed from materials selected from the group consisting of titanium alloy, cobalt-chromium beads, hydroxyapatite, aluminum oxide, ceramic materials, or combinations thereof.

5. The implant of claim 1 wherein said transition region has from about three to about five threads on the surface.

6. The implant of claim 1 wherein said neck has a rounded periphery.

7. The implant of claim 1 wherein said wrench-engaging projection has a hexagonal shape.

8. The implant of claim 1 wherein said bore is threaded to accommodate a retaining screw.

9. The implant of claim 1 wherein said implant further includes a cavity that protrudes from the bottom of said body into said body along the midline and terminates before reaching said bore so that a barrier remains between said cavity and said bore.

10. The implant of claim 9 wherein said implant further includes a through-hole that projects through the side walls of said body and through said cavity.

11. The implant of claim 1 wherein said transition region has a smooth surface.

12. The implant of claim 1 wherein said transition region has a surface which is beaded.

13. The implant of claim 1 wherein said transition region has a surface which is roughened.

* * * * *